US007781399B2

(12) United States Patent
Haynie

(10) Patent No.: US 7,781,399 B2
(45) **Date of Patent: *Aug. 24, 2010**

(54) IMMUNOGENIC COMPOSITIONS AND METHODS OF USE

(75) Inventor: Donald T. Haynie, Tampa, FL (US)

(73) Assignee: Artificial Cell Technologies, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/573,366

(22) Filed: Oct. 5, 2009

(65) Prior Publication Data

US 2010/0028410 A1 Feb. 4, 2010

Related U.S. Application Data

(63) Continuation of application No. 11/586,340, filed on Oct. 25, 2006, now Pat. No. 7,615,530.

(60) Provisional application No. 60/729,828, filed on Oct. 25, 2005.

(51) Int. Cl.
*A61K 38/00* (2006.01)

(52) U.S. Cl. ........................................................ 514/2

(58) Field of Classification Search ........................ None
See application file for complete search history.

(56) References Cited

U.S. PATENT DOCUMENTS

| | | | |
|---|---|---|---|
| 5,138,026 | A | 8/1992 | Miyasaka et al. |
| 5,629,213 | A | 5/1997 | Kornguth |
| 5,981,170 | A | 11/1999 | Trojnar |
| 6,020,175 | A | 2/2000 | Onda et al. |
| 6,479,146 | B1 | 11/2002 | Caruso et al. |
| 6,689,478 | B2 | 2/2004 | Laguitton |
| 6,743,521 | B2 | 6/2004 | Hubbell et al. |
| 6,833,192 | B1 | 12/2004 | Caruso et al. |
| 7,033,797 | B2 | 4/2006 | Jansen et al. |
| 7,045,146 | B2 | 5/2006 | Caruso et al. |
| 7,056,554 | B2 | 6/2006 | Voigt et al. |
| 7,101,575 | B2 | 9/2006 | Donath et al. |
| 2004/0013721 | A1 | 1/2004 | Antipov et al. |
| 2004/0241202 | A1 | 12/2004 | Chluba et al. |
| 2005/0069950 | A1 | 3/2005 | Haynie |
| 2005/0100883 | A1 | 5/2005 | Wang et al. |
| 2005/0180945 | A1 | 8/2005 | Chaikof et al. |

FOREIGN PATENT DOCUMENTS

| | | | |
|---|---|---|---|
| WO | 9308766 A1 | | 5/1993 |
| WO | WO 2006089572 A1 | * | 8/2006 |

OTHER PUBLICATIONS

Zhou et al. ("Protein microarrays on hybrid polymeric thin films prepared by self-assembly of polyelectrolytes for multiple-protein immunoassays," Proteomics 2006, 6, 1415-1426).*

Haynie, et al.; "Polypeptide Multilayer Films: Role of Molecular Structure and Charge"; Langmuir; 20; pp. 4540-4547; (2004).

Ai, et al.; "Biomedical Applications of Electrostatic Layer-by-Layer Nano-Assembly of Polymers, Enzymes, and Nanoparticles"; Cell Biochemistry and Biophysics; 39; pp. 23-43; 2003.

Boulmedais, et al; "Buildup of Exponentially Growing Multilayer Polypeptide Films with Internal Secondary Structure"; Langmuir; 19; pp. 440-445; 2003.

Boura, et al; "Endothelial Cells Grown on Thin Polyelectrolyte Mutilayered Films: An Evaluation of a New Versatile Surface Modification"; Biomaterials; 24; pp. 3521-3530; 2003.

Chluba et al; "Peptide Hormone Covalently Bound to Polyelectrolytes and Embedded into Mutilayer Architectures Conserving Full Biological Activity"; Biomacromolecules; 2; pp. 800-805; 2001.

Glinel, et al.; "Polyelectrolyte Multilayers Based on Amphiphilic Polysaccharides: Application for Entrapment and Release of Hydrophobic Molecules"; Abstracts of Papers American Chemical Society, 230, p. U3590; 2005; Abstract.

Haynie, et al.; "Protein-Inspired Multilayer Nanofilms: Science, Technology and Medicine"; Nanomedicine: Nanotechnology, Biology, and Medicine; 2; pp. 150-157; 2006.

Jessel, et al; "Bioactive Coatings Based on Polyelectrolyte Multilayer Architecture Functionalized by Embedded Proteins"; Adv. Mater.; 15; pp. 692-695; 2003.

Lavalle, et al; "Comparison of the Structure of Polyelectrolyte Multilayer Films Exhibiting a Linear and an Exponential Growth Regime: An in Situ Atomic Force Microscopy Study"; Macromolecules; 35; pp. 4458-4465; 2002.

Li, et al.; "Multilayer Biomimetics: Reversible Covalent Stabilization of a Nanostructured Biofilm"; Biomacromolecules; 5; pp. 1667-1670; 2004.

Picart, et al; "Buildup Mechanism for Poly(L-lysine)/Hyaluronic Acid Films onto a Solid Surface"; Langmuir; 17; pp. 7414-7424; 2001.

Picart, et al; "Molecular Basis for the Explanation of the Exponential Growth of Polyelectrolyte Multilayers"; PNAS; 22; pp. 12531-12535; 2002.

Richert, et al; "Cell Interactions with Polyeletrolyte Multilayer Films"; Biomacromolecules; 3; pp. 1170-1178; 2002.

Tryoen-Toth, et al; "Viability, Adhesion, and Bone Phenotype of Osteoblast-like Cells on Polyelectrolyte Multilayer Films"; J. Biomed. Mater. Res.; 60; pp. 657-667; 2002.

(Continued)

*Primary Examiner*—Christina Bradley
(74) *Attorney, Agent, or Firm*—Cantor Colburn LLP

(57) ABSTRACT

Disclosed herein are immunogenic compositions comprising a multilayer film comprising two or more layers of polyelectrolytes, wherein adjacent layers comprise oppositely charged polyelectrolytes. A first layer polyelectrolyte comprises an antigenic polypeptide comprising one or more surface adsorption regions covalently linked to one or more antigenic determinant regions, wherein the antigenic polypeptide and the one or more surface adsorption regions have the same polarity. The immunogenic compositions may be employed in methods of eliciting an immune response in a vertebrate organism.

17 Claims, 4 Drawing Sheets

OTHER PUBLICATIONS

Vautier, et al. "Polyelectrolyte Multilayer Films Moldulate Cytoskeletal Oranization in Chondrosarcoma Cells"; J. Biomater. Sol. Polymer Edn.; 13; pp. 713-732; 2002.
Zheng, et al.; "Design of Peptides for Thin Films, Coatings and Microcapsules for Applications in Biotechnology"; Journal of Biomaterials Science Polymer Edition 05; 16; pp. 285-299; 2005.
International Search Report; International Application No. PCT/US2006/041666; International Filing Date Oct. 25, 2006; Applicant's File Reference; Date of Mailing Jul. 4, 2007; Client Reference; 8 pages.
Written Opinion of International Searching Authority; International Application No. PCT/US2006/041666; International Filing Date Oct. 25, 2006; Applicant's File Reference; Date of Mailing Jul. 4, 2007; Client Reference; 9 pages.
Mozdzanowska, et al.; "Induction of Influenza Type A Virus-Specific Resistance by Immunization of Mice with a Synthetic Multiple Antigenic Peptide Vaccine that Contains Ectodomains of Matrix Proten 2"; Vaccine; 21; 2616-26; (2003).
Nadin, et al.; "Synthetic Malaria Peptide Vaccine Elicits High Levels of Antibodies in Vaccinees of Defined HLA Genotypes"; J. Infectious Diseases; 182; 1486-96; (2000).
Tam, et al.; "Vaccine Engineering: Enhancement of Immunogencity of Synthetic Peptide Vaccines Related to Hepatitis in Chemically Defined Models Consisting of T- and B-cell Epitopes"; Proc. Natl. Acad. Sci. USA; 86; 9084-88; (1989).
Wang, et al; "Effective Synthetic Peptide Vaccine for Foot-and-Mouth Disease in Swine"; Vaccine; 20; 2603-10; (2002).
Alcaro et al; "Synthetic Peptides in the Diagnosis of HIV Infection"; Current Protein and Peptide Science; 4; pp. 285-290; (2003).
Ben-Yedidia et al; "Design of Peptide and Polypeptide Vaccines"; Current Opinion in Biotechnology; 8; pp. 442-448; (1997).
Brown et al; "Optimisation of a Peptide-Based Indirect ELISA for the Detection of Antibody in the Serum of HIV-1 Seropositive Patients"; Journal of Immunological Methods; 200; pp. 79-88; (1997).
Decher, Gero; "Fuzzy Nanoassemblies: Toward Layered Polymeric Multicomposites"; Science; 277; pp. 1232-1237; (1997).
Giuliani et al; "A Universal Vaccine for Serogroup B Meningococcus"; Proc. Natl. Acad. Sci. USA; 103; pp. 10834-10839; (2006).
Humphreys et al; "Synthetic Peptide Vaccine Against Pandemic H5N1 Influenza Based on Ii-Key Modified MHC Class II Epitopes"; Pharmaceutical Discovery & Development; May/Jun. 2006; pp. 25, 26 and 29; (2006).
Iler, R. K.; "Multilayers of Colloidal Particles"; Journal of Colloid and Interface Science; 21; pp. 569-594; (1966).
Lvov, Y. et al; "Electrostatic Layer-by-Layer Assembly of Proteins and Polyions"; Protein Architecture: Interfacial Molecular Assembly and Immobilization Biotechnology; CRC Press; New York; 1528-1997; pp. 125-167; ISBN: 0824782364; (1999).
Lvov, Y. et al; "Urease Encapsulation in Nanoorganized Microshells"; Nano Letters; 1; pp. 125-128; (2001).

* cited by examiner

```
                          SEQUENCE LISTING

<160> NUMBER OF SEQ ID NOS: 12

<210> SEQ ID NO 1
<211> LENGTH: 24
<212> TYPE: PRT
<213> ORGANISM: Human adenovirus type 1

<400> SEQUENCE: 1

Asp Gln Gln Leu Leu Gly Ile Trp Gly Cys Ser Gly Lys Leu Ile Cys
1               5                   10                  15

Thr Thr Ala Val Pro Trp Asn Cys
            20


<210> SEQ ID NO 2
<211> LENGTH: 40
<212> TYPE: PRT
<213> ORGANISM: Artificial
<220> FEATURE:
<223> OTHER INFORMATION: The sequence was designed de novo and
      synthesized.

<400> SEQUENCE: 2

Lys Lys Lys Ala Lys Lys Lys Gly Lys Lys Lys Ala Lys Lys Lys Gly
1               5                   10                  15

Asp Gln Gln Leu Leu Gly Ile Trp Gly Cys Ser Gly Lys Leu Ile Cys
            20                  25                  30

Thr Thr Ala Val Pro Trp Asn Cys
        35                  40


<210> SEQ ID NO 3
<211> LENGTH: 16
<212> TYPE: PRT
<213> ORGANISM: Artificial
<220> FEATURE:
<223> OTHER INFORMATION: The sequence was designed de novo and
```

-continued synthesized.

<400> SEQUENCE: 3

Lys Lys Lys Ala Lys Lys Lys Gly Lys Lys Lys Ala Lys Lys Lys Gly
1 5 10 15

<210> SEQ ID NO 4
<211> LENGTH: 17
<212> TYPE: PRT
<213> ORGANISM: Human immunodeficiency virus type 1

<400> SEQUENCE: 4

Leu Gln Ala Arg Ile Leu Ala Val Glu Arg Tyr Leu Lys Asp Gln Gln
1 5 10 15

Leu

<210> SEQ ID NO 5
<211> LENGTH: 90
<212> TYPE: PRT
<213> ORGANISM: Artificial
<220> FEATURE:
<223> OTHER INFORMATION: The sequence was designed de novo and
synthesized.

<400> SEQUENCE: 5

Lys Lys Lys Ala Lys Lys Lys Gly Lys Lys Lys Ala Lys Lys Lys Gly
1 5 10 15

Asp Gln Gln Leu Leu Gly Ile Trp Gly Cys Ser Gly Lys Leu Ile Cys
20 25 30

Thr Thr Ala Val Pro Trp Asn Cys Gly Lys Lys Lys Ala Lys Lys Lys
35 40 45

Gly Lys Lys Lys Ala Lys Lys Lys Gly Leu Gln Ala Arg Ile Leu Ala
50 55 60

Val Glu Arg Tyr Leu Lys Asp Gln Gln Leu Lys Lys Lys Ala Lys Lys
65 70 75 80

Lys Gly Lys Lys Lys Ala Lys Lys Lys Gly
85 90

<210> SEQ ID NO 6
<211> LENGTH: 12
<212> TYPE: PRT
<213> ORGANISM: severe acute respiratory syndrome (SARS) virus

<400> SEQUENCE: 6

Tyr Ser Arg Val Lys Asn Leu Asn Ser Ser Glu Gly
1 5 10

<210> SEQ ID NO 7
<211> LENGTH: 85
<212> TYPE: PRT
<213> ORGANISM: Artificial
<220> FEATURE:
<223> OTHER INFORMATION: The sequence was designed de novo and
synthesized.

<400> SEQUENCE: 7

Lys Lys Lys Ala Lys Lys Lys Gly Lys Lys Lys Ala Lys Lys Lys Gly
1 5 10 15

Asp Gln Gln Leu Leu Gly Ile Trp Gly Cys Ser Gly Lys Leu Ile Cys
20 25 30

Thr Thr Ala Val Pro Trp Asn Cys Gly Lys Lys Lys Ala Lys Lys Lys
35 40 45

-continued

```
Gly Lys Lys Lys Ala Lys Lys Lys Gly Tyr Ser Arg Val Lys Asn Leu
    50                  55                  60

Asn Ser Ser Glu Gly Lys Lys Lys Ala Lys Lys Lys Gly Lys Lys Lys
65                  70                  75                  80

Ala Lys Lys Lys Gly
                85


<210> SEQ ID NO 8
<211> LENGTH: 18
<212> TYPE: PRT
<213> ORGANISM: Coccidioides immitis

<400> SEQUENCE: 8

Met Gln Phe Ser His Ala Leu Ile Ala Leu Val Ala Ala Gly Leu Ala
1               5                   10                  15

Ser Ala


<210> SEQ ID NO 9
<211> LENGTH: 34
<212> TYPE: PRT
<213> ORGANISM: Artificial
<220> FEATURE:
<223> OTHER INFORMATION: The sequence was designed de novo and
      synthesized.

<400> SEQUENCE: 9

Met Gln Phe Ser His Ala Leu Ile Ala Leu Val Ala Ala Gly Leu Ala
1               5                   10                  15

Ser Ala Lys Lys Lys Ala Lys Lys Lys Gly Lys Lys Lys Ala Lys Lys
            20                  25                  30

Lys Gly


<210> SEQ ID NO 10
<211> LENGTH: 26
<212> TYPE: PRT
<213> ORGANISM: Streptococcus mutans

<400> SEQUENCE: 10

Asn Ala Lys Ala Thr Tyr Glu Ala Ala Leu Lys Gln Tyr Glu Ala Asp
1               5                   10                  15

Leu Ala Ala Val Lys Lys Ala Asn Ala Ala
            20                  25


<210> SEQ ID NO 11
<211> LENGTH: 19
<212> TYPE: PRT
<213> ORGANISM: Streptococcus mutans

<400> SEQUENCE: 11

Ala Ala Leu Thr Ala Glu Asn Thr Ala Ile Lys Gln Arg Asn Glu Asn
1               5                   10                  15

Ala Lys Ala


<210> SEQ ID NO 12
<211> LENGTH: 79
<212> TYPE: PRT
<213> ORGANISM: Artificial
<220> FEATURE:
<223> OTHER INFORMATION: The sequence was designed de novo and
      synthesized.

<400> SEQUENCE: 12
```

-continued

```
Lys Lys Lys Ala Lys Lys Lys Gly Lys Lys Lys Ala Lys Lys Lys Gly
1               5                   10                  15

Asn Ala Lys Ala Thr Tyr Glu Ala Ala Leu Lys Gln Tyr Glu Ala Asp
            20                  25                  30

Leu Ala Ala Val Lys Lys Ala Asn Ala Ala Gly Ala Ala Leu Thr Ala
        35                  40                  45

Glu Asn Thr Ala Ile Lys Gln Arg Asn Glu Asn Ala Lys Ala Gly Lys
    50                  55                  60

Lys Lys Ala Lys Lys Lys Gly Lys Lys Lys Ala Lys Lys Lys Gly
65                  70                  75
```

IMMUNOGENIC COMPOSITIONS AND METHODS OF USE

CROSS-REFERENCE TO RELATED APPLICATION

This application is a continuation of U.S. application Ser. No. 11/586,340 filed Oct. 25, 2006, which claims the benefit of U.S. Provisional Application No. 60/729,828 filed Oct. 25, 2005, which is incorporated by reference herein.

BACKGROUND

Vaccines have been important in medicine ever since it was observed that, for certain diseases, initial exposure to the infectious agent conferred immunity against subsequent infections. Vaccines have been used for many years in order to build immunity in an individual against infection by particular pathogens such as viruses, bacteria, fungi, and parasites. Vaccines have also been used to stimulate the body's ability to mount an immune response against antigens on cancer cells, or against the formation of pathological fibrils. Vaccines can be administered via various routes including, for example, oral, intravenous, subcutaneous, transdermal, sublingual, intramuscular, and nasal administration.

Early vaccines relied on "live" or "killed" pathogens that retained their immunogenicity. A better understanding of the structure and function of particular pathogens and of the mechanisms of adaptive immunity has made it possible to design safer and more directed vaccines. For example, a current vaccine against the hepatitis B virus relies on inoculation using only a portion of the viral surface antigen, rather than the complete pathogen. Vaccines of this type have fewer side-effects, and they avoid the unwanted immune responses to antigens that are non-protective, i.e., do not confer lasting immunity. Vaccines have also been developed using recombinant DNA technology and gene therapy to provide DNA vaccines, which in favorable cases lead to a protective immune response.

Vaccination with protein antigens (e.g., from a viral protein or a tumor-specific antigen) or immunogenic polypeptides derived from protein antigens is a new strategy that has tremendous clinical potential because of its low toxicity and widespread applicability. Protein-based vaccines, however, have had only limited clinical success, due in part to difficulties with delivery. There is therefore a need to develop more efficacious means of engineering polypeptide-based antigens.

Currently, synthetic peptide vaccines are being evaluated for protection against bacteria, parasites, and viruses. Bacterial epitope vaccines include those directed against cholera and *shigella*. A synthetic vaccine against malaria has undergone Phase I and Phase II clinical trials. Influenza and hepatitis B represent two viral systems in which synthetic peptide vaccines look especially promising, and there has been much interest recently in the development of synthetic vaccines against human immunodeficiency virus-1 (HIV-1).

A desirable immune response to a protein or peptide antigen in a vaccine context includes both humoral and cellular-mediated immunity. The humoral component involves the stimulation of B cells, which produce antibodies, while the cell-mediated component involves T lymphocytes. Cytotoxic T-lymphocytes (CTLs) play an important role in the cell-mediated immune system, lysing virally-infected or bacterially-infected cells. Specifically, CTLs possess cell surface receptors, which can recognize foreign peptides associated with MHC class I and/or class II molecules.

There is a need for methods and specialized delivery platforms suitable for the delivery of complex antigens such as polypeptides to vertebrate organisms. The engineering of immunogenic polypeptides and structures made of immunogenic polypeptides are promising for this purpose. Preferably, the resulting presentation of immunogenic determinants will activate at least some components of the adaptive immune system, i.e., antigen presentation will eliciting a sufficient immune response for combating a particular pathogen, whether the immune response is mediated by antibodies, cytotoxic T cells, helper T cells, natural killer cells, or macrophages, or some combination thereof.

SUMMARY

In one embodiment, an immunogenic composition comprises a multilayer film comprising two or more layers of polyelectrolytes, wherein adjacent layers comprise oppositely charged polyelectrolytes, wherein a first layer polyelectrolye comprises an antigenic polypeptide comprising one or more surface adsorption regions covalently linked to one or more antigenic determinant regions. The antigenic polypeptide and the one or more surface adsorption regions have the same polarity. The one or more surface adsorption regions comprises one or more amino acid sequence motifs, the one or more amino acid sequence motifs consisting of 5 to 15 amino acids and having a magnitude of net charge per residue of greater than or equal to 0.4. The one or more antigenic determinant regions comprise 3 to about 250 amino acid residue. The antigenic polypeptide is not a homopolymer, is at least 15 amino acids long, and has an aqueous solubility at pH 4 to 10 of greater than 50 μg/mL. Also, a second layer comprises a second layer polyelectrolyte comprising a polycationic material or a polyanionic material having a molecular weight of greater than 1,000 and at least 5 charges per molecule, and a charge opposite that of the first layer polypeptide.

In another embodiment, a method of eliciting an immune response in a vertebrate organism comprises administering into the vertebrate organism the above-described immunogenic composition.

DETAILED DESCRIPTION

Figure 1:
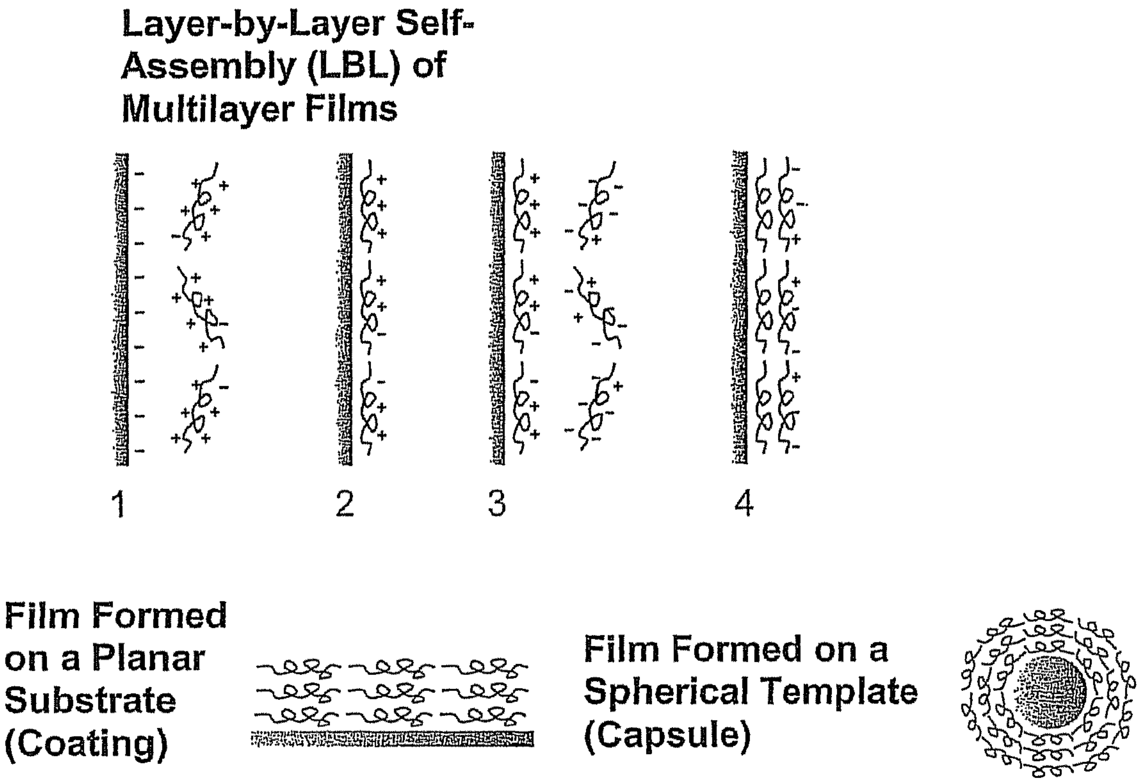
FIG. 1 shows a schematic of the assembly of oppositely charged polypeptides.

The present invention is directed to immunogenic compositions and methods of eliciting an immune response in a vertebrate organism with the immunogenic compositions.

As used herein, "layer" means a thickness increment, e.g., on a template for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments.

The term "polyelectrolyte" includes polycationic and polyanionic materials having a molecular weight of greater than 1,000 and at least 5 charges per molecule. Suitable polycationic materials include, for example, polyamines. Polyamines include, for example, a polypeptide, polyvinyl amine, poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly(diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide, a nucleic acid, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acids" means the 20 common naturally occurring L-amino acids, that is, glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan, and proline.

"Non-natural amino acid" means an amino acid other than any of the common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

"Amino acid sequence motif" means a contiguous amino acid sequence comprising n residues, wherein n is 5 to 15. In one embodiment, the magnitude of the net charge per residue of an amino acid sequence motif is greater than or equal to 0.4. In another embodiment, the magnitude of the net charge per residue of an amino acid sequence motif is greater than or equal to 0.5. As used herein, the magnitude of the net charge refers to the absolute value of the net charge, that is, the net charge can be positive of negative.

As used herein "peptide" and "polypeptide" all refer to a series of amino acids connected one to the other by peptide bonds between the alpha-amino and alpha-carboxy groups of adjacent amino acids, and may contain or be free of modifications such as glycosylation, side chain oxidation, or phosphorylation, provided such modifications, or lack thereof, do not destroy immunogenicity. As used herein, the term "peptide" is meant to refer to both a peptide and a polypeptide or protein.

"Designed polypeptide" means a polypeptide comprising one or more amino acid sequence motifs, wherein the polypeptide is at least 15 amino acids in length and the ratio of the number of charged residues of the same polarity minus the number of residues of the opposite polarity to the total number of residues in the polypeptide is greater than or equal to 0.4 at pH 7.0. In other words, the magnitude of the net charge per residue of the polypeptide is greater than or equal to 0.4. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the polypeptide, in general, designed polypeptides suitable for ELBL deposition have a practical upper length limit of 1,000 residues.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α-helix, β-sheet, and β-turn.

"Polypeptide multilayer film" means a film comprising one or more designed polypeptides as defined above. For example, a polypeptide multilayer film comprises a first layer comprising a designed polypeptide and a second layer comprising a polyelectrolyte having a net charge of opposite polarity to the designed polypeptide. For example, if the first layer has a net positive charge, the second layer has a net negative charge; and of the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, etc. A substrate surface can be regular or irregular. A substrate can be a crystal. A substrate can be a bioactive molecule. Substrates range in size from the nanoscale to the macro-scale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine-formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "microcapsule" is a polyelectrolyte film in the form of a hollow shell or a coating surrounding a core. The core comprises a variety of different encapsulants, for example, a protein, a drug, or a combination thereof.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film is a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an antigen is an entity that elicits an immune response. The human body fights infection and inhibits reinfection by increasing the number of antibodies in the bloodstream and elsewhere.

"Antigen" means a foreign substance that elicits an immune response (e.g., the production of specific antibody molecules) when introduced into the tissues of a susceptible vertebrate organism. An antigen contains one or more epitopes. The antigen may be a pure substance, a mixture of substances (including cells or cell fragments). The term antigen includes a suitable antigenic determinant, auto-antigen, self-antigen, cross-reacting antigen, alloantigen, tolerogen, allergen, hapten, and immunogen, or parts thereof, and combinations thereof, and these terms are used interchangeably. Antigens are generally of high molecular weight and commonly are polypeptides. Antigens that elicit strong immune responses are said to be strongly immunogenic. The site on an antigen to which a complementary antibody may specifically bind is called an epitope or antigenic determinant.

"Antigenic" refers to the ability of a composition to give rise to antibodies specific to the composition or to give rise to a cell-mediated immune response.

As used herein, the terms "epitope" and "antigenic determinant" are used interchangeably and mean the structure or sequence of an antigen, e.g., a protein or a designed peptide, which is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein. A "conformational epitope" involves amino acid residues from different portions of the linear sequence of a protein that come into contact in the three-dimensional structure of the protein. For efficient interaction to occur between the antigen and the antibody, the epitope must be readily available for binding. Thus, the epitope or antigenic determinants are present in the antigen's native, cellular environment, or only exposed when denatured. In their natural form they may be cytoplasmic (soluble), membrane associated, or secreted. The number, location and size of the epitopes will depend on how much of the antigen is presented during the antibody making process.

As used herein, a "vaccine composition" is a composition, which elicits an immune response in a mammal to which it is administered and which protects the immunized organism against subsequent challenge by the immunizing agent or an immunologically cross-reactive agent. Protection can be complete or partial with regard to reduction in symptoms or infection as compared with a non-vaccinated organism. An immunologically cross-reactive agent can be, for example, the whole protein (e.g., glucosyltransferase) from which a subunit peptide has been derived for use as the immunogen. Alternatively, an immunologically cross-reactive agent can be a different protein, which is recognized in whole or in part by antibodies elicited by the immunizing agent.

As used herein, an "immunogenic composition" is intended to encompass a composition, which elicits an immune response in an organism to which it is administered and which may or may not protect the immunized mammal against subsequent challenge with the immunizing agent. In one embodiment, an immunogenic composition is a vaccine composition.

The present invention is includes both vaccine compositions and immunogenic compositions comprising a polyelectrolye multilayer film comprising a charged antigenic polypeptide having one or more antigenic determinants.

Polyelectrolyte multilayer films are thin films (e.g., a few nanometers to millimeters thick) composed of alternating layers of oppositely charged polyelectrolytes. Such films can be formed by layer-by-layer assembly on a suitable substrate. In electrostatic layer-by-layer self-assembly ("ELBL"), the physical basis of association of polyelectrolytes is electrostatics. Film buildup is possible because the sign of the surface charge density of the film reverses on deposition of successive layers. The general principle of ELBL deposition of oppositely charged polyions is illustrated in FIG. 1. The generality and relative simplicity of the ELBL film process permits the deposition of many different types of polyelectrolyte onto many different types of surface. Polypeptide multilayer films are a subset of polyelectrolyte multilayer films, comprising at least one layer comprising a charged polypeptide. A key advantage of polypeptide multilayer films is environmental benignity. ELBL films can also be used for encapsulation.

Applications of polypeptide films and microcapsules include, for example, nano-reactors, biosensors, artificial cells, and drug delivery vehicles.

The design principles for polypeptides suitable for electrostatic layer-by-layer deposition are elucidated in U.S. Patent Publication No. 2005/0069950, incorporated herein by reference. Briefly, the primary design concerns are the length and charge of the polypeptide. Electrostatics is the most important design concern because it is the basis of ELBL. Without suitable charge properties, a polypeptide will not be substantially soluble in aqueous solution at pH 4 to 10 and cannot readily be used for the fabrication of a multilayer film by ELBL. Other design concerns include the physical structure of the polypeptides, the physical stability of the films formed from the polypeptides, and the biocompatibility and bioactivity of the films and the constituent polypeptides.

As defined above, a designed polypeptide means a polypeptide comprising one or more amino acid sequence motifs, wherein the polypeptide is at least 15 amino acids in length and the magnitude of the net charge per residue of the polypeptide is greater than or equal to 0.4 at pH 7.0. "Amino acid sequence motif" means a contiguous amino acid sequence comprising n residues, wherein n is 5 to 15. Positively-charged (basic) naturally-occurring amino acids at pH 7.0 are Arg, His, and Lys. Negatively-charged (acidic) naturally-occurring amino acid residues at pH 7.0 are Glu and Asp. An amino acid motif comprising a mixture of amino acid residues of opposite charge can be employed so long as the overall ratio of charge meets the specified criteria. In one embodiment, a designed polypeptide is not a homopolymer.

In one exemplary embodiment, the amino acid sequence motif comprises 7 amino acids. Four charged amino acids is a suitable minimum for a motif size of 7, because fewer than 4 charges yields decreased peptide solubility and decreased control over ELBL. Further, regarding biocompatibility, each identified amino acid sequence motif in genomic data is long enough at 7 residues to constitute a continuous epitope, but not so long as to correspond substantially to residues both on the surface of a protein and in its interior. Thus, the charge and length of the amino acid sequence motif help to ensure that a sequence motif identified in genomic data is likely to occur on the surface of the folded protein from which the sequence motif is derived. In contrast, a very short motif could appear to the body to be a random sequence, or one not specifically "self," and therefore elicit an immune response.

In some cases, a design concern regarding amino acid sequence motifs and designed polypeptides is their propensity to form secondary structures, notably α-helix or β-sheet. In some embodiments, it is desirable to be able to control, e.g., minimize, secondary structure formation by the designed polypeptides in an aqueous medium in order to maximize control over thin film layer formation. First, it is preferred that sequence motifs be relatively short, that is about 5 to about 15 amino acids, because long motifs are more likely to adopt a stable three-dimensional structure in solution. Second, a linker, such as a glycine or proline residue, covalently joined between successive amino acid sequence motifs in a designed polypeptide will reduce the propensity of the polypeptide to adopt secondary structure in solution. Glycine, for example, has a very low α-helix propensity and a very low β-sheet propensity, making it energetically very unfavorable for a glycine and its neighboring amino acids to form regular secondary structure in aqueous solution. Third, the α-helix and β-sheet propensity of the designed polypeptides themselves can be minimized by selecting amino acid sequence motifs for which the summed α-helix propensity is less than 7.5 and the summed β-sheet propensity is less than 8. "Summed" propensity means the sum of the α-helix or β-sheet propensities of all amino acids in a motif. Amino acid sequence motifs having a somewhat higher summed α-helix propensity and/or summed β-sheet propensity are suitable for ELBL, particularly when joined by linkers such as Gly or Pro. In certain applications, the propensity of a polypeptide to form secondary structure can be relatively high as a specific design feature of thin film fabrication. The secondary structure propensities for all 20 naturally occurring amino acids can be calculated using the method of Chou and Fasman (see P. Chou and G. Fasman Biochemistry 13:211 (1974), which is incorporated by reference herein in its entirety).

Another design concern is control of the stability of polypeptide ELBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides within the same layer or in adjacent layers can increase structural strength. Sulfydryl-containing amino acids include cysteine and homocysteine. In addition, a sulfhydryl can be added to β-amino acids such as D,L-β-amino-β-cylohexyl propionic acid; D,L-3-aminobutanoic acid; or 5-(methylthio)-3-aminopentanoic acid. Sulfhydryl-containing amino acids can be used to "lock" (bond together) and "unlock" layers of a multilayer polypeptide film by a change in oxidation potential. Also, the incorporation of a sulfhydryl-containing amino acid in a sequence motif of a designed polypeptide enables the use of relatively short peptides in thin film fabrication, by virtue of intermolecular disulfide bond formation. Amino acid sequence motifs containing sulfhydryl-containing amino acids may be selected from a library of motifs identified using the methods described below, or designed de novo.

In one embodiment, the designed sulfhydryl-containing polypeptides, whether synthesized chemically or produced in a host organism, are assembled by ELBL in the presence of a reducing agent to prevent premature disulfide bond formation. Following film assembly, the reducing agent is removed and an oxidizing agent is added. In the presence of the oxidizing agent disulfide bonds form between sulfhydryls groups, thereby "locking" together the polypeptides within layers and between layers where thiol groups are present. Suitable reducing agents include dithiothreitol ("DTT"), 2-mercaptoethanol (2-ME), reduced glutathione, tris(2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitro-benzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

Biocompatibility is a design concern in biomedical applications. In such applications, genomic or proteomic information is used as a basis for polymer design to yield, ideally, "immune inert" polypeptides. The approach will be particularly useful if the fabricated or coated object will make contact with circulating blood. Because the amino acid sequence motifs are highly polar, they typically occur on the surface of the native folded form of the protein from which they are derived. The "surface" is that part of a folded protein that is in contact with the solvent or inaccessible to the solvent solely because of the granular nature of water. Amino acid sequence motifs identified in blood proteins are effectively always in contact with cells and molecules of the immune system while the protein is in the blood. Therefore, polypeptides derived from the surface of folded blood proteins are less likely to be immunogenic than sequences selected at random. Designed polypeptides will generally be biocompatible, but the extent of immune response or any other type of biological response may well depend on specific details of a sequence motif.

Bioactivity can be incorporated into a film, coating or microcapsule by a number of methods. For example, a designed polypeptide comprising the film can comprise a functional domain. Alternatively, bioactivity may be associated with another bioactive molecule encapsulated or coated by the polypeptide thin film. In one embodiment, the template comprises a bioactive molecule such as a protein crystal.

A functional domain in this context is an independently thermostable region of a protein that has specific biofunctionality (e.g., binding phosphotyrosine). In a multi-domain protein, multiple functional domains may exist, as for example in the protein tensin, which encompasses a phosphotyrosine binding domain and a protein tyrosine phosphatase domain. The inclusion of a functional domain in a designed polypeptide incorporated into a multilayer film can provide the film with a desired functionality, including, for example, specific ligand binding, targeting in vivo, biosensing, and biocatalysis.

The bioactive molecule can be a protein, a functional fragment of a protein, a functional fragment of a protein that is not part of a designed polypeptide, a complex of proteins, an oligopeptide, an oligonucleotide, a nucleic acid, a ribosome, an active therapeutic agent, a phospholipid, a polysaccharide, a lipopolysaccharide, a functional membrane fragment, a membrane structure, a virus, a pathogen, a cell, an aggregate of cells, an organelle, a lipid, a carbohydrate, a pharmaceutical, or an antimicrobial agent. The bioactive molecule can be in the form of a well-ordered or amorphous crystal. The protein can be an enzyme or an antibody. The substrate can comprise the bioactive molecule. In one embodiment, the substrate has a bioactive molecule disposed on its surface prior to deposition of layers of oppositely charged polypeptides. In another embodiment, the substrate is a crystal comprising the bioactive molecule.

In one embodiment, amino acid sequence motifs are designed de novo. In other embodiments, amino acid sequence motifs are selected from the genomic or proteomic information of a specific organism, such as the human genome. For example, the primary structure of complement C3 (gi|68766) or lactotransferrin (gi|4505043) can be used to search for amino acid sequence motifs in a human blood protein.

A method of identifying a first amino acid sequence motif in a polypeptide comprises selecting a starter amino acid residue in the polypeptide; examining an amino acid sequence comprising the starter amino acid residue and the following n−1 amino acid residues in the polypeptide for occurrences of positive and negative charges, wherein n is 5 to 15; determining the 5-15 amino acid residues as an amino acid sequence motif if the net charge of the side chains of the 5-15 amino acid residues at pH 7 is greater than or equal to 0.4*n; or discarding the sequence if the net charge of the side chains of the 5-15 amino acid residues at pH 7 is less than 0.4*n.

In one embodiment, the process of searching protein sequence data for a negatively charged amino acid sequence motif of length n comprising only amino acids that are neutral or negatively charged is described as follows. First, a first amino acid residue is selected in a protein sequence. Second, this amino acid residue and the following n−1 amino acid residues are examined for occurrences of arginine (Arg), histidine (His), or lysine (Lys) (the three naturally occurring amino acids that may be positively charged at neutral pH), where n is 5 to 15. Third, if one or more Arg, His, or Lys residues is found in these n amino acid residues, the process is begun anew at a second amino acid residue. If, however, no Arg, His, or Lys is found in these n residues, the n residues are examined to determine the number of occurrences of glutamate (Glu) and/or aspartate (Asp) (the two negatively charged amino acids at neutral pH). Fourth, if there are at least 0.4*n occurrences of Glu and/or Asp in the n residues, the sequence is cataloged as a negatively charged amino acid sequence motif. If, however, fewer than 0.4*n occurrences of negatively charged amino acids are found, the sequence beginning with the first amino acid residue is discarded and the process is begun anew, for example, at a second amino acid residue immediately adjacent to the first amino acid residue. After cataloging a motif, the process can begin anew at a second amino acid residue.

The process for identifying a positively charged sequence motif is analogous to searching protein sequence data for an n residue-long amino acid sequence comprising only amino acids that are neutral or positively charged, and for which the magnitude of the net charge of the amino acid residue side chains at neutral pH is greater than or equal to 0.4*n.

Also analogous is the process for identifying a negatively charged amino acid sequence motif or a positively charged amino acid sequence motif of length n, allowing both positively and negatively charged amino acid residues in the motif. For example, the procedure for identifying a positively charged amino acid sequence motif of length n would be to select a first amino acid residue in a polypeptide. Next, examine this amino acid residue and the following n−1 amino acids residues for occurrences of residues that are positively or negatively charged at pH 7. Determine the net charge of the n amino acid residue side chains. If the absolute value of the net charge is less than 0.4*n, then the sequence is discarded and a new search is begun at another amino acid, while if the absolute value of the net charge is greater than or equal to 0.4*n, then the sequence is an amino acid sequence motif. The motif will be positive if net charge is greater than zero and negative if the net charge is less than zero.

De novo design of amino acid sequence motifs as presently defined follows essentially similar rules, except that the sequences are not limited to those found in nature. A length of motif n and a desired sign and magnitude of net charge are chosen. Then, n amino acids are selected for the amino acid sequence motif that result in the desired sign and magnitude of charge, so that the absolute value of the net charge of the n amino acids is greater than or equal to 0.4*n. A potential advantage of de novo design of an amino acid sequence motif is that the practitioner can select from among all amino acids (the 20 naturally occurring ones and all non-natural amino acids) to achieve the desired net charge, rather than being limited to the amino acids found in a particular known protein sequence. The larger pool of amino acids enlarges the potential range of physical, chemical and/or biological characteristics that can be selected in designing the sequence of the motif compared to identification of an amino acid sequence motif in a genomic sequence.

A designed polypeptide as presently defined will comprise one or more amino acid sequence motifs. The same motif may be repeated, or different motifs may be joined in designing a polypeptide for ELBL. In one embodiment, the amino acid sequence motifs are covalently joined with no intervening sequence. In another embodiment, a designed polypeptide comprises two or more amino acid sequence motifs covalently joined by a linker. The linker can be amino acid based, e.g., one or more amino acid residues such as glycine or proline, or it can be any other compound suitable for covalently linking two amino acid sequence motifs. In one embodiment, a linker comprises 1-4 amino acid residues, for example, 1-4 glycine and/or proline resides. The linker comprises a suitable length or composition so that the designed polypeptide is maintained at a net charge per residue that is greater than or equal to 0.4.

In one embodiment, a designed polypeptide is greater than or equal to 15 amino acid residues long. In other embodiments, a designed polypeptide is greater than 18, 20, 25, 30, 32 or 35 amino acids long. 1,000 residues is a practical upper bound on polymer length.

Once amino acid sequence motifs have been selected or designed de novo, a designed polypeptide with amino acid-based linkers is synthesized using methods well known in the art, such as solid phase synthesis and F-moc chemistry, or heterologous expression in bacteria following gene cloning and transformation. Designed polypeptides may be synthesized by a peptide synthesis company, for example, SynPep Corp. (Dublin, Calif.), produced in the laboratory using a peptide synthesizer, or produced by recombinant DNA methods. Any development of novel methods of peptide synthesis could enhance the production of peptides but would not fundamentally change peptide design as described herein.

A method of making a designed polypeptide multilayer film comprises depositing a plurality of layers of oppositely charged chemical species on a substrate, wherein at least one layer comprises a designed polypeptide. Successively deposited polyelectrolytes will have opposite net charges. FIG. 1 is a schematic illustrating ELBL deposition. In one embodiment, deposition of a designed polypeptide (or other polyelectrolyte) comprises exposing the substrate to an aqueous solution comprising a designed polypeptide (or other polyelectrolyte) at a pH at which it has a suitable net charge for ELBL. In other embodiments, the deposition of a designed polypeptide or other polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the ELBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure by deposition includes forming aqueous solutions of the polyions at a pH at which they are ionized (i.e., pH 4-10), providing a substrate bearing a surface charge, and alternating immersion of the substrate into the charged polyelectrolyte solutions. The substrate is optionally washed in between deposition of alternating layer.

The concentration of polyion suitable for deposition of the polyion can readily be determined by one of ordinary skill in the art. An exemplary concentration is 0.1 to 10 mg/mL. Typically, the thickness of the layer produced is substantially independent of the solution concentration of the polyion during deposition in the stated range. For typical non-polypeptide polyelectrolytes such as poly(acrylic acid) and poly(allylamine hydrochloride), typical layer thicknesses are about 3 to about 5 Å, depending on the ionic strength of solution. Short polyelectrolytes typically form thinner layers than long polyelectrolytes. Regarding film thickness, polyelectrolyte film thickness depends on humidity as well as the number of layers and composition of the film. For example, PLL/PLGA films 50 nm thick shrink to 1.6 nm upon drying with nitrogen. In general, films of 1 nm to 100 nm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly (acrylic acid) and poly(allylamine hydrochloride), films comprising a single bilayer of oppositely charged polyelectrolyte can be stable.

It is contemplated that an immune response may be elicited via presentation of any protein or peptide capable of eliciting such a response. In one embodiment, the antigen is a key epitope, which gives rise to a strong immune response to a particular agent of infectious disease, i.e., an immunodominant epitope. If desired, more than one antigen or epitope may be included in the immunogenic composition in order to increase the likelihood of an immune response.

In one embodiment, a multilayer film comprises a first layer antigenic polypeptide comprising one or more surface adsorption regions covalently linked to one or more antigenic determinant regions, wherein the first layer antigenic polypeptide and the one or more surface adsorption regions have the same net polarity. The surface adsorption regions comprise one or more amino acid sequence motifs. The first layer antigenic polypeptide is at least 15 amino acids long, and has a solubility in aqueous solution at pH 4 to 10 of greater than 50 μg/mL. In one embodiment, the one or more surface adsorption regions and the one or more antigenic determinant regions have the same net polarity. In another embodiment, the solubility of the first layer antigenic polypeptide at pH 4 to 10 is greater than or equal to about 1 mg/mL. The solubility is a practical limitation to facilitate deposition of the polypeptides from aqueous solution. A practical upper limit on the degree of polymerization of an antigenic polypeptide is about 1,000 residues. It is conceivable, however, that longer composite polypeptides could be realized by an appropriate method of synthesis.

Figure 2:
FIG. 2 illustrates an embodiment of an antigenic polypeptide comprising one antigenic determinant region (3) and two surface adsorption regions (1,2), one attached to the N-terminus of the antigenic determinant region (1) and one attached to the C-terminus of the antigenic determinant region (2).

In one embodiment, an antigenic polypeptide comprises a single antigenic determinant (3) flanked by two surface adsorption regions, a N-terminal surface adsorption region (1) and a C-terminal surface adsorption region (2). (FIG. 2)

Figure 3:
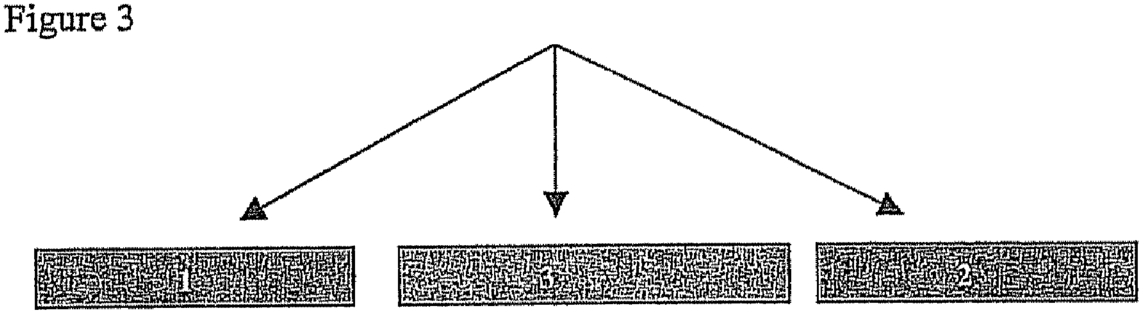
FIG. 3 illustrates independent preparation of the three different regions of an antigenic polypeptide for LBL by solution-phase synthesis, solid-phase synthesis, or recombinant peptide production.

Each of the independent regions (e.g., antigenic determinant regions (1) and surface adsorption regions (2,3)) of the antigenic polypeptide can be synthesized separately by solution-phase synthesis, solid-phase synthesis, or genetic engineering of a suitable host organism. (FIG. 3) Solution-phase synthesis is the method used for production of most of the approved peptide pharmaceuticals on the market today. The solution-phase method can be used to synthesize relatively long peptides and even small proteins. The longest peptides that have made by the solution-phase method are calcitonins (32 mers). More commonly, the method is used to produce small- or medium-length peptides in quantities of up to hundreds of kilograms. It is possible to produce such large quantities of the desired peptides in a facility that follows good manufacturing practices.

Alternatively, the various independent regions can be synthesized together as a single polypeptide chain by solution-phase synthesis, solid-phase synthesis, or genetic engineering of a suitable host organism. The choice of approach in any particular case will be a matter of convenience or economics.

Figure 4:
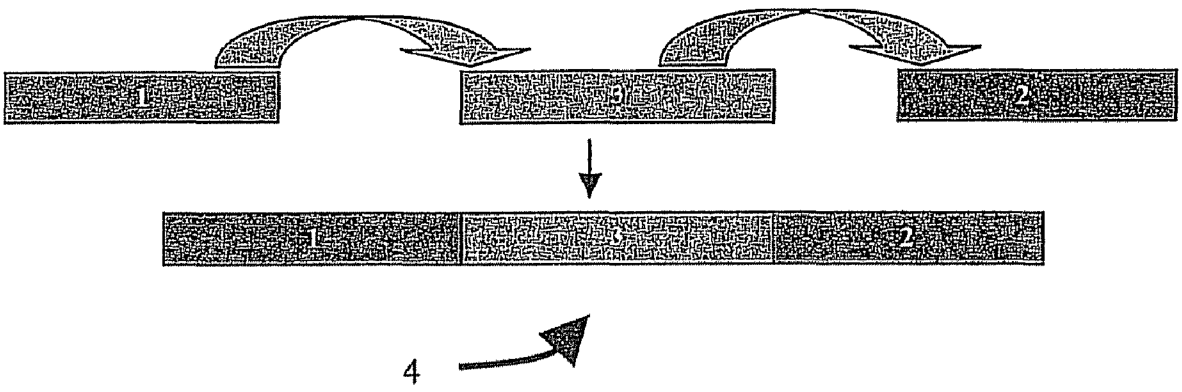
FIG. 4 illustrates joining of three regions of the antigenic peptide (4).

If the various antigenic determinant regions and surface adsorption regions are synthesized separately (FIG. 3), once purified, for example, by ion exchange chromatography followed by high-performance liquid chromatography, they are joined by peptide bond synthesis (FIG. 4). That is, the N-terminal surface adsorption region (1), the antigenic determinant region (3) and the C-terminal antigenic determinant region (2) are covalently joined to produce the antigenic polypeptide (4). The approach is similar to so-called hybrid synthesis, wherein peptide segments with fully protected side chains are synthesized by the solid-phase technique and then joined by peptide bonds in a solution-phase or solid-phase procedure. This hybrid approach has been applied to the synthesis of T20, a 36-amino acid residue peptide, but it has not been widely exploited.

Figure 5:
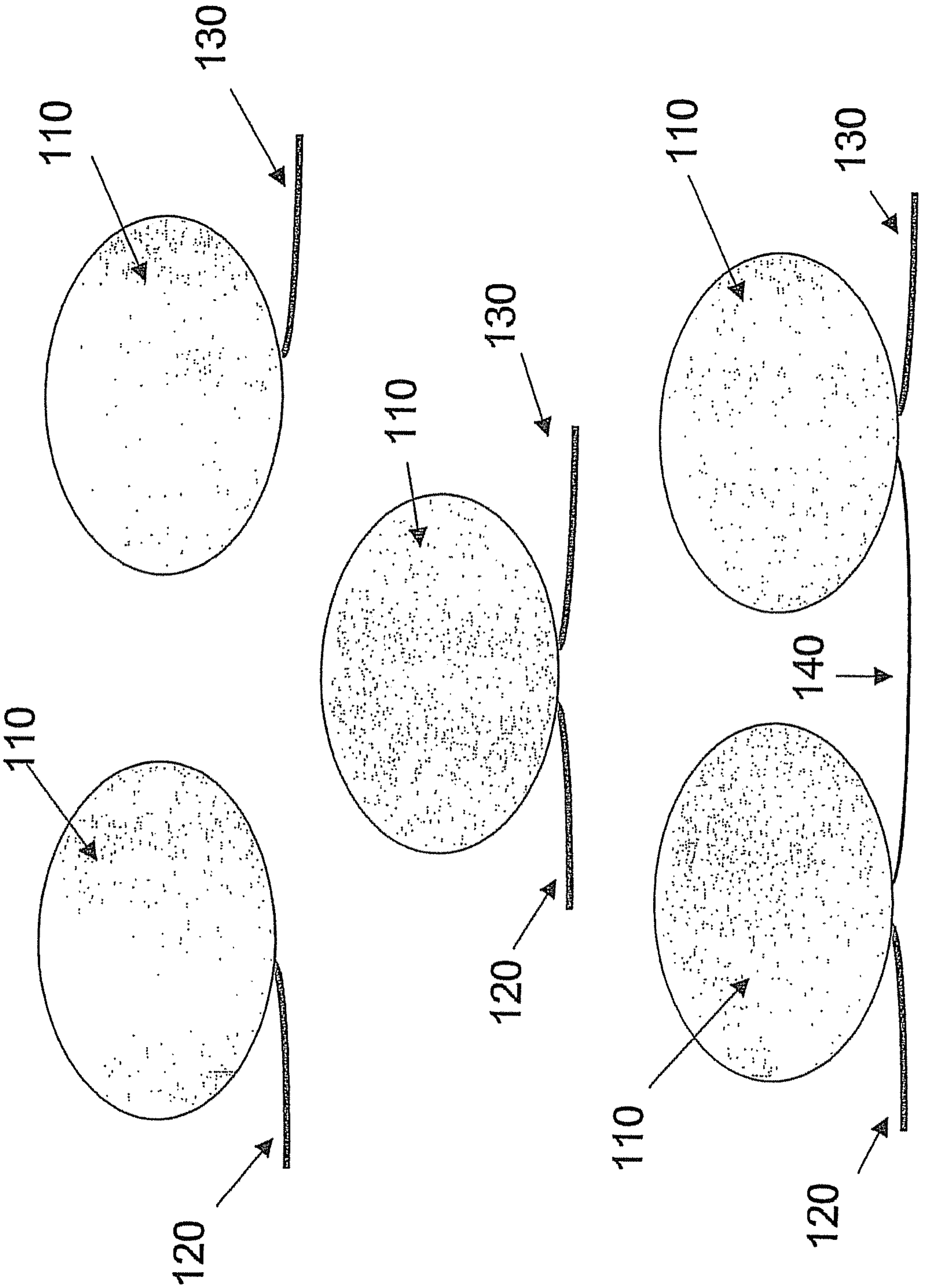
FIG. 5 illustrates an embodiment of an antigenic polypeptide comprising two surface adsorption regions (120 and 130) and one antigenic determinant region (110).

FIG. 5 illustrates an embodiment of an antigenic polypeptide comprising two surface adsorption regions (120 and 130) and one antigenic determinant region (110). 120 is the N-terminal surface absorption region. 130 is the C-terminal absorptive region. Each surface adsorption region comprises one or more amino acid sequence motifs. An antigenic polypeptide is a unique combination of surface adsorption region(s) and antigenic determinant region(s) in a single polypeptide chain. Linker peptide sequences (140) can be used to generate a composite polypeptide comprising antigenic determinant regions in a single polypeptide chain. In one embodiment, antigenic determinant region (110) is a small functional region comprising from about 50 to about 130 amino acid residues, and having a diameter of about 2 nm. In an alternate embodiment, antigenic determinant region (110) is a large functional region comprising about 250 amino acid residues, and having a diameter of about 4 nm. The length of 16 amino acid residues in extended conformation is approximately 5.5 nm.

In one embodiment, an antigenic polypeptide comprises one antigenic determinant region and one surface adsorption region, wherein the surface adsorption region comprises two amino acid sequence motifs. In another embodiment, an antigenic polypeptide comprises one antigenic determinant region and two surface adsorption regions, one attached to the N-terminus of the antigenic determinant region and one attached to the C-terminus of the antigenic determinant region, wherein each surface adsorption region comprises one or more amino sequence motifs and the two surface adsorption regions are the same or different and have the same polarity. (FIG. 2) The purpose of the surface adsorption region(s) is to enable adsorption of the polypeptide onto an oppositely charged surface in order to build a multilayer film.

The number of surface adsorption regions in an antigenic polypeptide relative to the number and/or length of the antigenic determinant regions is related to the solubility requirement. For example, if the antigenic determinant region is a short amino acid sequence of, for example, three amino acid residues, only one amino acid sequence motif of at least 12 amino acid residues will be required to adsorb the antigenic polypeptide onto a suitably charged surface. If, by contrast, the antigenic determinant region is a soluble folded structural domain of a protein comprising, for example, 120 amino acid residues, two amino acid sequence motifs will typically be sufficient to impart enough charge for the antigenic polypeptide to be water soluble and suitable for adsorption. The motifs could be contiguous and located at the N terminus of the domain, contiguous and located at the C-terminus of the domain, or noncontiguous with one at the N-terminus and one at the C-terminus.

The combined length of the surface adsorption regions is related more to the dissipation due to thermal energy, which must be overcome for antigenic peptide adsorption to occur spontaneously, than the number amino acid residues in the antigenic determinant region of the antigenic polypeptide. Therefore, increasing the degree of polymerization of the antigenic determinant region by a factor of two does not necessarily require surface adsorption regions twice as long for effective binding of the surface adsorption regions of the antigenic polypeptide. The physical basis of adsorption of an antigenic polypeptide to a surface is electrostatic attraction (and release of counterions to bulk solution), the precise mass of the domain is of secondary importance on the length scale of nanometers, and the main "force" counteracting antigenic polypeptide adsorption is thermal energy. In view of this, one of skill in the art can readily design surface adsorption regions that are suitable for physical adsorption to a surface of the particular antigenic determinant region of interest.

An antigenic determinant region comprises 3 to about 250 amino acid residues. The term antigenic determinant region includes both antigenic motifs and antigenic domains. Antigenic motifs are relatively short and therefore generally do not have a compact three-dimensional fold; nevertheless, they can exhibit specific antigenicity. While antigenic motifs generally do not have a compact three-dimensional fold, they can comprise elements of secondary structure such as α-helices and β-sheets. When the antigenic determinant region is an antigenic motif, it will typically comprise 3 to about 50 amino acid residues. When the antigenic determinant region is an antigenic domain, it will typically comprise about 50 to about 250 amino acid residues.

An antigenic domain is defined herein as at least a portion of a polypeptide which, when folded, creates its own hydrophobic core. A native protein, for example, may contain a plurality of structural domains, each of which acts as an independent unit of structure and function. The biological function of one domain can be completely independent of the function of another, as in the case of a catalytic domain and a binding domain in the same polypeptide chain, where the two domains do not interact with each other at all. Structural interactions between domains in a native protein are not only possible, but relatively common; in such cases the interaction between one structural domain and another structural domain can be viewed as a type of quaternary structure.

As used herein, an antigenic domain typically has a minimum of about 50 amino acid residues and a maximum of about 250 amino acid residues. In principle, any antigenic domain from a protein can be employed in an antigenic peptide as outlined herein so long as the antigenic polypeptide has the appropriate aqueous solubility for ELBL deposition. In one embodiment, the antigenic domain has a water solubility at pH 4 to 10 of greater than 50 μg/mL. In another embodiment, the antigenic domain has a water solubility at pH 4 to 10 of greater than or equal to 1 mg/mL. In yet another embodiment, the first layer antigenic polypeptide comprises at least two amino acid sequence motifs when the antigenic determinant region comprises an antigenic domain.

The antigenic polypeptide, when it comprises an antigenic motif instead of a functional domain, will typically have an magnitude of the net charge per residue of greater than or equal to 0.4. If, however, the antigenic motif has a net charge per residue of less than 0.4, the one or more surface adsorption regions will typically have a magnitude of the net charge per residue of greater than 0.4 to compensate and give the antigenic polypeptide the appropriate charge properties for solubility and physical adsorption.

A polypeptide or antigen may contain one or more distinct antigenic determinants. An antigenic determinant may refer to an immunogenic portion of a multichain polypeptide.

The antigenic polypeptide as described herein comprises an antigenic determinant region. Suitable antigenic determinant regions include viral antigens, bacterial antigens, fungal antigens, parasite antigens, tumor antigens, antigens involved in autoimmunity, and combinations comprising one or more of the foregoing antigenic determinant regions.

In one embodiment, the antigenic determinant region comprises a viral antigen. Suitable viral antigens include, but are not limited to, retroviral antigens such as HIV-1 antigens including the gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1-NS2A, 80% E, and other Japanese encephalitis viral antigen components; rabies viral antigens such as rabies glycoprotein, rabies nucleoprotein and other rabies viral antigen components; and combinations comprising one or more of the foregoing antigenic determinant regions.

In another embodiment, the antigenic determinant region comprises a bacterial antigen. Suitable bacterial antigens include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens; *Mycobacterium tuberculosis* bacterial antigens such as heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, and other pneumococcal bacterial antigen components; *haemophilus influenza* bacterial antigens; anthrax bacterial antigens such as anthrax protective antigen and other anthrax bacterial antigen components; rickettsiae bacterial antigens such as romps and other rickettsiae bacterial antigen components; and combinations comprising one or more of the foregoing antigenic determinant regions.

In another embodiment, the antigenic determinant region comprises a fungal antigen. Suitable fungal antigens include, but are not limited to, candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components, and tinea fungal antigens such as trichophytin and other *coccidiodes* fungal antigen components; and combinations comprising one or more of the foregoing antigenic determinant regions.

In another embodiment, the antigenic determinant region comprises a parasite antigen. Suitable protozoal and other parasitic antigens include, but are not limited to, *plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; *toxoplasma* antigens such as SAG-1, p30 and other *toxoplasma* antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components; and combinations comprising one or more of the foregoing parasite antigens.

In one embodiment, the antigenic determinant region comprises a tumor antigen. Suitable tumor antigens include, but are not limited to, prostate specific antigen (PSA), telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells; and combinations comprising one or more of the foregoing tumor antigens. It is contemplated that antigens from any type of tumor cell can be used in the compositions and methods described herein.

In another embodiment, the antigenic determinant region comprises an antigen involved in autoimmunity. Suitable antigens which have been shown to be involved in autoimmunity include, but are not limited to, myelin basic protein, myelin oligodendrocyte glycoprotein and proteolipid protein of multiple sclerosis and CII collagen protein of rheumatoid arthritis; and combinations comprising one or more of the foregoing antigenic determinant regions.

Knowledge of antigenic determinants or epitopes for antigens of the pathogen of the target disease can be a useful starting point for the development of synthetic peptide vaccines. The more that is known about a pathogen, its mechanisms of action, and how the immune system responds to infection, the better the odds of preparing a successful vaccine. Complete determination of the structure of the genome of a pathogen is a routine and rapid procedure which can aid in the determination of antigenic determinant sites for know pathogens.

Methods and techniques for determining the location and composition of an antigenic determinant or epitope for a specific antibody are well known in the art. These techniques can be used to identify and/or characterize epitopes for use as antigenic determinant regions. In one embodiment, mapping/characterization methods of an epitope for an antigen specific antibody can be determined by epitope "foot-printing" using chemical modification of the exposed amines/carboxyls in the antigenic protein. One example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry.

In another embodiment, a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectra of the complex compared to the spectra of the free antigen, and the amino acids involved in the binding may be identified that way.

In another embodiment, epitope mapping/characterization may be done by peptide scanning. In this approach, a series of overlapping peptides spanning the full-length of the polypeptide chain of an antigen are prepared and tested individually with regard to immunogenicity. The antibody titer of the corresponding peptide antigen is determined by a standard method, e.g., enzyme-linked immunosorbent assay. The various peptides can then be ranked with regard to immunogenicity, providing an empirical basis for selection of peptide design for vaccine development.

In another embodiment, protease digestion techniques may also be useful in the context of epitope mapping and identification. Antigenic determinant-relevant regions/sequences may be determined by protease digestion, e.g. by using trypsin in a ratio of about 1:50 to antigenic protein overnight (0/N) digestion at 37° C. and pH 7-8, followed by mass spectrometry (MS) analysis for peptide identification. The peptides protected from trypsin cleavage by the antigenic protein may subsequently be identified by comparison of samples subjected to trypsin digestion and samples incubated with CD38BP and then subjected to digestion by e.g. trypsin (thereby revealing a foot print for the binder). Other enzymes like chymotrypsin, pepsin, etc. may also or alternatively be used in a similar epitope characterization method. Moreover, protease digestion can provide a quick method for determining the location of a potential antigenic determinant sequence within a known antigenic protein using a known antibody.

The invention is further directed to an immunogenic composition, said immunogenic composition comprising a multilayer film comprising two or more layers of polyelectrolytes, wherein adjacent layers comprise oppositely charged polyelectrolytes, wherein a first layer polyelectrolye comprises an antigenic polypeptide. The immunogenic composition optionally further comprises one or more layers comprising additional antigenic polypeptides.

In one embodiment, an immunogenic composition comprises a plurality of antigenic determinant regions, either on the same or different antigenic polypeptides. The plurality of antigenic determinants may be from the same or different infectious agents. In one embodiment, the immunogenic composition comprises a plurality of unique antigenic polypeptides. In another embodiment, the immunogenic composition comprises a plurality of immunogenic peptides comprising multiple antigenic determinant regions within each polypeptide. In another embodiment, the polypeptide is a conjugated peptide comprising an antigenic peptide mixture conjugated to a lipid moiety, or conjugated to a carrier protein moiety. An advantage of these immunogenic compositions is that multiple antigenic determinants or multiple conformations of a single linear antigenic determinant can be present in a single synthetic vaccine particle. Such compositions with multiple antigenic determinants can potentially yield antibodies against multiple epitopes, increasing the odds that at least some of the antibodies generated by the immune system of the organism will neutralize the pathogen or target specific antigens on cancer cells, for example.

In one embodiment, the immunogenic composition comprises a plurality of antigenic polypeptides, wherein each of the antigenic polypeptides is an immunogen of the same pathogen. Optionally, the immunogenic composition includes a plurality of antigenic polypeptides directed to different epitopes of the same pathogen. The different epitopes are optionally found in regions in close proximity on the pathogen surface. Thus, in one embodiment, the first layer polyelectrolyte comprises two or more antigenic determinants. In another embodiment, the multilayer film comprises a second antigenic polypeptide comprising one or more second surface adsorption regions covalently linked to one or more second antigenic determinant regions, wherein the second antigenic polypeptide and the one or more second surface adsorption regions have the same polarity, wherein the one or more second surface adsorption regions comprises one or more second amino acid sequence motifs, the one or more second amino acid sequence motifs consisting of 5 to 15 amino acids and having a magnitude of net charge per residue of greater than or equal to 0.4, and wherein the one or more second antigenic determinant regions comprises 3 to about 250 amino acid residues, wherein the second antigenic polypeptide is not a homopolymer, is at least 15 amino acids long, and has an aqueous solubility at pH 4 to 10 of greater than 50 μg/ml.

The immunogenicity of an immunogenic composition may be enhanced in a number of ways. In one embodiment, the multilayer film optionally comprises one or more additional immunogenic bioactive molecules. Although not necessary, the one or more additional immunogenic bioactive molecules will typically comprise one or more additional antigenic determinants. Suitable additional immunogenic bioactive molecules include, for example, a drug, a protein, an oligonucleotide, a nucleic acid, a lipid, a phospholipid, a carbohydrate, a polysaccharide, a lipopolysaccharide, or a combination comprising one or more of the foregoing bioactive molecules. Other types of additional immune enhancers include a functional membrane fragment, a membrane structure, a virus, a pathogen, a cell, an aggregate of cells, an organelle, or a combination comprising one or more of the foregoing bioactive structures.

In one embodiment, the multilayer film optionally comprises one or more additional bioactive molecules. The one or more additional bioactive molecule can be a drug. Alternatively, the immunogenic composition is in the form of a hollow shell or a coating surrounding a core. The core comprises a variety of different encapsulants, for example, one or more additional bioactive molecules, including, for example, a drug. Thus, the immunogenic compositions designed as described herein could also be used for combined therapy, e.g., eliciting an immune response and for targeted drug delivery. Micron-sized "cores" of a suitable therapeutic material in "crystalline" form can be encapsulated by immunogenic composition comprising the antigenic polypeptides, and the resulting microcapsules could be used for drug delivery. The core may be insoluble under some conditions, for instance high pH or low temperature, and soluble under the conditions where controlled release will occur. The surface charge on the crystals can be determined by 4-potential measurements (used to determine the charge in electrostatic units on colloidal particles in a liquid medium). The rate at which microcapsule contents are released from the interior of the microcapsule to the surrounding environment will depend on a number of factors, including the thickness of the encapsulating shell, the antigenic polypeptides used in the shell, the presence of disulfide bonds, the extent of cross-linking of peptides, temperature, ionic strength, and the method used to assemble the peptides. Generally, the thicker the capsule, the longer the release time.

In another embodiment, the additional immunogenic biomolecule is a nucleic acid sequence capable of directing host organism synthesis of a desired immunogen or interfering with the expression of genetic information from a pathogen. In the former case, such a nucleic acid sequence is, for example, inserted into a suitable expression vector by methods known to those skilled in the art. Expression vectors suitable for producing high efficiency gene transfer in vivo include retroviral, adenoviral and vaccinia viral vectors. Operational elements of such expression vectors include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence. In the latter case, multiple copies of such a nucleic acid sequence will be prepared for delivery, for example, by encapsulation of the nucleic acids within a polypeptide multilayer film in the form of a capsule for intravenous delivery.

In construction of a recombinant expression vector, it should additionally be noted that multiple copies of the nucleic acid sequence of interest (either E1 or core) and its attendant operational elements may be inserted into each vector. In such an embodiment, the host organism would produce greater amounts per vector of the desired E1 or core protein. The number of multiple copies of the nucleic acid sequence which may be inserted into the vector is limited only by the ability of the resultant vector due to its size, to be transferred into and replicated and transcribed in an appropriate host microorganism.

In a further embodiment, the immunogenic composition comprises a mixture of antigenic peptides/immunogenic bioactive molecules. These may be derived from the same antigen, they may be different antigens from the same infectious agent or disease, or they may be from different infectious agents or diseases. The complex or mixture will therefore raise an immune response against a number of antigens and possibly a number of infectious agents or diseases as specified by the antigenic peptide/protein components of the delivery system.

In one embodiment, the immunogenic composition evokes a response from the immune system to a pathogen. In one embodiment, a vaccine composition comprises an immunogenic composition in combination with a pharmaceutically acceptable carrier. Thus a method of vaccination against a pathogenic disease comprises the administering to a subject in need of vaccination an effective amount of the immunogenic composition.

Pharmaceutically acceptable carriers include, but are not limited to, large, slowly metabolized macromolecules such as proteins, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes can also be used as carriers.

A method of eliciting an immune response against a disease or pathogen in a vertebrate (e.g., vaccination) comprises administering an immunogenic composition comprising a multilayer film comprising an antigenic polypeptide. In one embodiment, the antigenic polypeptide is in the most exterior or solvent-exposed layer of the multilayer film. The immunogenic composition can be administered orally, intranasally, intravenously, intramuscularly, subcutaneously, intraperitoneally, sublingually, or transdermally, either with or without a booster dose. Generally, the compositions are administered in a manner compatible with the dosage formulation, and in such amount as will be prophylactically and/or therapeutically effective. Precise amounts of immunogenic composition to be administered depend on the judgment of the practitioner and may be peculiar to each subject. It will be apparent to those of skill in the art that the therapeutically effective amount of an immunogenic composition will depend, inter alia, upon the administration schedule, the unit dose of antigen administered, whether the compositions are administered in combination with other therapeutic agents, and the immune status and health of the recipient. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

The invention is further illustrated by the following non-limiting examples.

EXAMPLES

Example 1

Vaccine Composition for HIV-1 with a Single Antigenic Determinant

The antigenic polypeptide comprises a single antigenic determinant region, wherein the antigenic determinant region is a polypeptide sequence from a pathogen and the surface adsorption region is located at the N-terminus of the antigenic determinant region. In one example, the antigenic determinant region is an antigenic determinant in a known pathogen, e.g., HIV-1, e.g., peptide ARP7022, or DQQLLGIWGCSGKLICTTAVPWNC (SEQ ID NO: 1). A suitable antigenic polypeptide comprises:

(SEQ ID NO: 2)
KKKAKKKGKKKAKKKGDQQLLGIWGCSGKLICTTAVPWNC

The surface adsorption region of the antigenic peptide comprises KKKAKKKGKKKAKKKG (SEQ ID NO: 3). The 24-residue ARP7022 sequence (SEQ ID NO. 1) represents a conserved immunodominant region of HIV-1 glycoprotein 41 (residues 593-616) and is recognized by most European and African HIV+ sera (Lange et al. (1993) AIDS 7, 461). The full-length peptide corresponding to SEQ ID NO. 2 is synthesized by one of any means known in the art. Artificial viruses are prepared with this peptide a number of ways, e.g., by depositing by LBL immunogenic compositions comprising 5 bilayers of poly(L-lysine) and poly(L-glutamic acid) and a final layer of the peptide corresponding to SEQ ID NO. 2 onto 3-μm diameter microparticles of calcium carbonate. The artificial viruses prepared in this way have an exterior or surface exposed layer which is formed of multiple copies of the immunogenic peptide represented by SEQ ID NO. 2. The polypeptide concentration for adsorption of each layer is 2 mg-mL$^{-1}$ in an aqueous solution at pH 7. The adsorption time for each layer is 20 min. Microparticles are "rinsed" between each peptide adsorption step by centrifugation. In some cases, the calcium carbonate template particles of the final artificial virus construct are dissolved by treatment with EDTA. The structures thus prepared can be referred to as artificial viruses or synthetic vaccines: They "display" on their surface antigenic determinants, in the present case multiple copies of an antigenic determinant known to elicit an immune response that generates antibodies which recognize intact HIV-1. The technology is promising for preventative medicine and HIV-1 treatment.

Example 2

Vaccine Composition for HIV-1 with Multiple Antigenic Determinants

There are two main types of immunogenic compositions with multiple antigenic determinants: 1) Each antigenic polypeptide adsorbed simultaneously comprises an identical plurality of antigenic determinant regions, wherein the antigenic determinant regions of the polypeptide are the same or different and the antigenic determinant regions are based on the same or a different pathogen, and 2) Multiple antigenic peptides adsorbed simultaneously each comprise one of a plurality of functional units, wherein the functional regions are or are not based on the same pathogen. It is important to mention that mixed solutions of the two types of peptide are, in principle, no less useful for fabrication of the surface layer of an artificial virus than solutions of one indicated type or the other. The surface adsorption regions of either type will ordinarily but need not be identical from peptide to peptide. Moreover, the surface adsorption regions can be located at the N-terminus of the composite antigenic peptide, at the C-terminus, between functional regions in the same composite peptide, or some combination of these possibilities.

Type 1 immunogenic composition with multiple antigenic determinants. In this example, the antigenic polypeptide comprises two antigenic sequences in the antigenic determinant region, wherein both of the antigenic sequences are from a the same pathogen and there are surface adsorption regions located at the N-terminus of the antigenic determinant region, at the C-terminus of the antigenic determinant region, and between the antigenic sequences. In one example, the antigenic determinants are from a known pathogen, e.g., HIV-1, e.g., peptide ARP7022, or DQQLLGIWGCSGKLICTTAVPWNC (SEQ ID NO: 1), and LQARILAVERYLKDQQL (SEQ ID NO:4). A suitable antigenic polypeptide comprises:

(SEQ ID NO: 5)
KKKAKKKGKKKAKKKGDQQLLGIWGCSGKLICTTAVPWNCGKKKA

KKKGKKKAKKKGLQARILAVERYLKDQQLKKKAKKKGKKKAKKKG

The surface adsorption regions of the composite antigenic peptide comprise KKKAKKKGKKKAKKKG (SEQ ID NO: 3). SEQ ID NO. 4 corresponds to residues 67-83 of HIV-1 glycoprotein 41. As before, the full-length peptide corresponding to SEQ ID NO. 5 is synthesized by one of any means known in the art. Artificial viruses are prepared with this peptide a number of ways, e.g., by depositing by LBL immunogenic compositions comprising 5 bilayers of poly(L-lysine) and poly(L-glutamic acid) and a final layer of the peptide corresponding to SEQ ID NO. 5 onto 3-μm diameter microparticles of calcium carbonate. The artificial viruses prepared in this way have an exterior or surface exposed layer which is formed of multiple copies of the immunogenic peptide represented by SEQ ID NO. 5. The polypeptide concentration for adsorption of each layer is 2 mg-mL$^{-1}$ in an aqueous solution at pH 7. The adsorption time for each layer is 20 min. Microparticles are "rinsed" between each peptide adsorption step by centrifugation. In some cases, the calcium carbonate template particles of the final artificial virus construct are dissolved by treatment with EDTA. The structures thus prepared can be referred to as artificial viruses or synthetic vaccines: They "display" on their surface antigenic determinants, in the present case multiple copies of an antigenic determinant known to elicit an immune response that generates antibodies which recognize intact HIV-1. The technology is promising not only for preventative medicine and for HIV-1 therapy, but also cancer therapy (when the antigenic sequences represent cancer cell surface markers).

Example 3

Immunogenic Composition for HIV-1 and SARS

The antigenic polypeptide comprises two antigenic determinant regions and two surface adsorption regions, wherein the antigenic determinant regions are polypeptide sequences from a single pathogen and the surface adsorption regions are located at the N-terminus and C-terminus of the antigenic polypeptide and the first antigenic determinant region is separated from the central surface adsorption region a short linker. In one example, one antigenic determinant region is a known antigenic determinant in a pathogen, e.g., HIV-1, e.g., peptide ARP7022, or DQQLLGIWGCSGKLICTTAVPWNC (SEQ ID NO: 1), and the other antigenic determinaqt region, viz., YSRVKNLNSSEG (SEQ ID NO:6), is from a putative envelope protein from severe acute respiratory syndrome (SARS) virus, and the short linker is a single glycine residue, G:

(SEQ ID NO: 7)
KKKAKKKGKKKAKKKGDQQLLGIWGCSGKLICTTAVPWNCGKKKA

KKKGKKKAKKKGYSRVKNLNSSEGKKKAKKKGKKKAKKKG

As before, the surface adsorption regions of the composite antigenic peptide each comprise KKKAKKKGKKKAKKKG (SEQ ID NO: 3).

Example 4

Vaccine Composition for a Fungus with a Single Antigenic Determinant

The antigenic polypeptide comprises a single antigenic determinant region, wherein the antigenic determinant region is a polypeptide sequence from a pathogen and the surface adsorption region is located at the C-terminus of the antigenic determinant region. In one example, the antigenic determinant region is a signal sequence in a protein, e.g., Ag2/PRA, of a pathogen, e.g., *Coccidioides immitis*, e.g., MQFSHALIALVAAGLASA (SEQ ID NO: 8). A suitable antigenic polypeptide comprises:

```
MQFSHALIALVAAGLASAKKKAKKKGKKKAKKKG   (SEQ ID NO: 9)
```

The surface adsorption region of the antigenic peptide comprises KKKAKKKGKKKAKKKG (SEQ ID NO: 3). The 18-residue sequence from Ag2/PRA (SEQ ID NO. 8) represents a region of *Coccidioides immitis*, the causative agent of coccidioidomycosis (San Joaquin Valley fever), a respiratory disease. The full-length peptide corresponding to SEQ ID NO. 9 is synthesized by one of any means known in the art. Multilayer films are prepared with this peptide a number of ways, e.g., by depositing by LBL immunogenic compositions comprising 5 bilayers of poly(L-lysine) and poly(L-glutamic acid) and a final layer of the peptide corresponding to SEQ ID NO. 9 onto 3-μm diameter microparticles of calcium carbonate. The films prepared in this way have an exterior or surface exposed layer which is formed of multiple copies of the immunogenic peptide represented by SEQ ID NO. 9. The polypeptide concentration for adsorption of each layer is 2 mg-mL in an aqueous solution at pH 7. The adsorption time for each layer is 20 min. Microparticles are "rinsed" between each peptide adsorption step by centrifugation. In some cases, the calcium carbonate template particles of the final artificial virus construct are dissolved by treatment with EDTA. The structures thus prepared can be referred to as artificial viruses or synthetic vaccines: They "display" on their surface antigenic determinants, in the present case multiple copies of an antigenic determinant known to elicit an immune response that generates antibodies which recognize intact *Coccidioides immitis*. The technology is promising for preventative medicine and *Coccidioides immitis* treatment.

Example 5

Vaccine Composition for a Bacterium with Multiple Antigenic Determinants

The antigenic polypeptide comprises a single antigenic determinant region, wherein the antigenic determinant region comprises two polypeptide sequences from a pathogenic bacterium and the surface adsorption regions are located at the C-terminus of the antigenic determinant region, at the N-terminus of the antigen determinant region, and between the two sequences from the pathogenic bacterium. In one example, the antigenic determinants are from a protein, e.g., the surface protein antigen PAc from *Streptococcus mutans* MT8148, e.g., NAKATYEAALKQYEADLAAVKKANAA (SEQ ID NO: 10) and AALTAENTAIKQRNENAKA (SEQ ID NO: 11). A suitable antigenic polypeptide comprises:

```
                                    (SEQ ID NO: 12)
KKKAKKKGKKKAKKKGNAKATYEAALKQYEADLAAVKKANAAGA
ALTAENTAIKQRNENAKAGKKKAKKKGKKKAKKKG
```

The surface adsorption regions of the antigenic peptide comprise KKKAKKKGKKKAKKKG (SEQ ID NO: 3). The sequences from the PAc gene product (SEQ ID NO. 10 and SEQ ID NO. 11) represent a portion of the alanine-rich repeating region in the surface protein antigen, which has received much attention as an antigenic component for vaccines against dental caries. The full-length peptide corresponding to SEQ ID NO. 12 is synthesized by one of any means known in the art. Multilayer films are prepared with this peptide a number of ways, e.g., by depositing by LBL immunogenic compositions comprising 5 bilayers of poly(L-lysine) and poly(L-glutamic acid) and a final layer of the peptide corresponding to SEQ ID NO. 12 onto 3-μm diameter microparticles of calcium carbonate. The films prepared in this way have an exterior or surface exposed layer which is formed of multiple copies of the immunogenic peptide represented by SEQ ID NO. 12. The polypeptide concentration for adsorption of each layer is 2 $mg\text{-}mL^{-1}$ in an aqueous solution at pH 7. The adsorption time for each layer is 20 min. Microparticles are "rinsed" between each peptide adsorption step by centrifugation. In some cases, the calcium carbonate template particles of the final artificial virus construct are dissolved by treatment with EDTA. The structures thus prepared can be referred to as artificial viruses or synthetic vaccines: They "display" on their surface antigenic determinants, in the present case multiple copies of an antigenic determinant known to elicit an immune response that generates antibodies which recognize intact *S. mutans*. The technology is promising for preventative medicine and *S. mutans* treatment.

In summary, the artificial viruses fabricated with immunogenic peptides by ELBL demonstrate the following advantages. Synthetic peptide vaccines eliminate the need for certain vaccine safety tests, reducing the cost and risk of vaccine production. For example, the specific toxicity test is used to detect incomplete inactivation of virions for vaccines involving attenuated or killed virus particles, for example, by cell culture analysis, saving time and resources. A vaccine construct that does not use a virus or other type of pathogen as the immunogen eliminates the need for such safety tests. In addition, since mammalian cell culture is not needed to propagate viruses for the invention, the risk of contamination of the present vaccine with unwanted material from a virus, microorganism, or eukaryote is extremely low, particularly if the synthetic peptides and artificial viruses are produced under GMP conditions.

Additional advantages of the presently claimed invention include simplicity of fabrication and rapid response by virtue of the "cassette" approach to synthesis of peptides suitable for LBL.

Moreover, the approach enables multiple conformations of a single linear antigenic determinant to be "displayed" simultaneously on the surface of single synthetic vaccine particle, yielding antibodies against multiple conformations of the sequence and thereby increasing the odds that at least some of the antibodies generated by the immune system of the organism will neutralize the pathogen or target specific antigens on cancer cells. As stated above, it is envisioned that peptides containing different functional regions could be incorporated into a single synthetic vaccine construct, increasing the spectrum of protection: The presently claimed synthetic vaccine can present multiple antigenic determinants directed to multiple pathogens, providing protection against many different pathogens in a single vaccination.

The synthetic vaccine platform is extremely general and, in principle, can work for any pathogen. Thus, unlike other known vaccination approaches, which require engineering of genes, transfer of the genes to a suitable expression host, expression of the genes, purification of the recombinant protein or virus particles, etc., the synthetic vaccines disclosed herein can provide for a decreased response time to the threat of a pathogen.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A multilayer film comprising two or more layers of polyelectrolytes, wherein adjacent layers comprise oppositely charged polyelectrolytes, wherein a first layer polyelectrolye comprises a first antigenic polypeptide comprising one or more surface adsorption regions covalently linked to one or more antigenic determinant regions, wherein the first antigenic polypeptide and the one or more surface adsorption regions have the same polarity, wherein the one or more surface adsorption regions comprise one or more amino acid sequence motifs, the one or more amino acid sequence motifs consisting of 5 to 15 amino acid residues and having a magnitude of net charge per residue of greater than or equal to 0.4 at neutral pH, and wherein the one or more antigenic determinant regions comprise 3 to about 250 amino acid residues, and one or more antigenic determinant regions comprise an antigen involved in autoimmunity, wherein the antigen is selected from the group consisting of myelin basic protein, myelin oligodendrocyte glycoprotein, the proteolipid protein of multiple sclerosis and the CII collagen protein of rheumatoid arthritis, wherein the first antigenic polypeptide is an unbranched polypeptide, is not a homopolymer, is at least 15 amino acid residues long, and has an aqueous solubility at pH 4 to 10 of greater than 50 μg/ml;

wherein a second layer comprises a second layer polyelectrolyte comprising a polycationic material or a polyanionic material having a molecular weight of greater than 1,000 and at least 5 charges per molecule, and a charge opposite that of the first layer polypeptide.

2. The multilayer film of claim 1, wherein the first antigenic polypeptide is in the exterior layer of the multilayer film.

3. The multilayer film of claim 1, wherein the first antigenic polypeptide comprises two or more antigenic determinant regions.

4. The multilayer film of claim 3, wherein the two or more antigenic determinant regions are from the same or different pathogen or target disease.

5. The multilayer film of claim 1, further comprising a second antigenic polypeptide comprising one or more second surface adsorption regions covalently linked to one or more second antigenic determinant regions, wherein the second antigenic polypeptide and the one or more second surface adsorption regions have the same polarity, wherein the one or more second surface adsorption regions comprise one or more second amino acid sequence motifs, the one or more second amino acid sequence motifs consisting of 5 to 15 amino acids and having a magnitude of net charge per residue of greater than or equal to 0.4 at neutral pH, and wherein the one or more second antigenic determinant regions comprise 3 to about 250 amino acid residues, wherein the second antigenic polypeptide is not a homopolymer, is at least 15 amino acids long, and has an aqueous solubility at pH 4 to 10 of greater than 50 μg/ml.

6. The multilayer film of claim 5, wherein the one or more first antigenic determinant regions and the one or more second antigenic determinant regions are from the same or different autoimmune antigen.

7. The multilayer film of claim 1, further comprising a drug, an oligonucleotide, a nucleic acid, a lipid, a phospholipid, a carbohydrate, a polysaccharide, a lipopolysaccharide, or a combination of one or more of the foregoing molecules.

8. The multilayer film of claim 1, wherein the first antigenic polypeptide has an aqueous solubility of greater than or equal to about 1 mg/mL.

9. The multilayer film of claim 1, wherein the one or more antigenic determinant regions are antigenic motifs comprising 3 to about 50 amino acid residues, and wherein the first antigenic polypeptide has a magnitude of charge per residue at neutral pH of greater than or equal to 0.4.

10. The multilayer film of claim 1, wherein the one or more antigenic determinant regions are antigenic domains comprising about 50 to about 250 amino acid residues.

11. The multilayer film of claim 10, wherein the antigenic domains have a water solubility at pH 4 to 10 of greater than 50 μg/mL.

12. The multilayer film of claim 1, wherein the multilayer film encapsulates one or more non-peptide molecules.

13. The multilayer film of claim 1, wherein the multilayer film is in the form of a microcapsule.

14. The multilayer film of claim 13, wherein the microcapsule comprises a core comprising a drug, a protein, an oligonucleotide, a nucleic acid, a lipid, a phospholipid, a carbohydrate, a polysaccharide, a lipopolysaccharide, or a combination of one or more of the foregoing molecules.

15. A method of eliciting an immune response in a vertebrate organism comprising administering into the vertebrate organism a composition comprising, a multilayer film comprising two or more layers of polyelectrolytes, wherein adjacent layers comprise oppositely charged polyelectrolytes, wherein a first layer polyelectrolye comprises a first antigenic polypeptide comprising one or more surface adsorption regions covalently linked to one or more antigenic determinant regions, wherein the first antigenic polypeptide and the one or more surface adsorption regions have the same polarity, wherein the one or more surface adsorption regions comprise one or more amino acid sequence motifs, the one or more amino acid sequence motifs consisting of 5 to 15 amino acid residues and having a magnitude of net charge per residue of greater than or equal to 0.4 at neutral pH, and wherein the one or more antigenic determinant regions comprise 3 to about 250 amino acid residues, and one or more antigenic determinant regions comprise an antigen involved in autoimmunity, wherein the antigen is selected from the group consisting of myelin basic protein, myelin oligodendrocyte glycoprotein, the proteolipid protein of multiple sclerosis and the CII collagen protein of rheumatoid arthritis, wherein the first antigenic polypeptide is an unbranched polypeptide, is not a homopolymer, is at least 15 amino acid residues long, and has an aqueous solubility at pH 4 to 10 of greater than 50 μg/ml;

wherein a second layer comprises a second layer polyelectrolyte comprising a polycationic material or a polyanionic material having a molecular weight of greater than 1,000 and at least 5 charges per molecule, and a charge opposite that of the first layer polypeptide.

16. The method of claim 15, wherein the multilayer film is administered intramuscularly or subcutaneously.

17. A method of making a multilayer film, the method comprising:

depositing a first layer polyelectrolyte on a surface of a substrate to form a first layer; wherein, the first layer polyelectrolye comprises a first antigenic polypeptide comprising one or more surface adsorption regions covalently linked to one or more antigenic determinant regions, wherein the first antigenic polypeptide and the one or more surface adsorption regions have the same polarity, wherein the one or more surface adsorption regions comprise one or more amino acid sequence motifs, the one or more amino acid sequence motifs consisting of 5 to 15 amino acid residues and having a magnitude of net charge per residue of greater than or equal to 0.4 at neutral pH, and wherein the one or more antigenic determinant regions comprise 3 to about 250 amino acid residues, and one or more antigenic determinant regions comprise an antigen involved in autoimmunity, wherein the antigen is selected from the group consisting of myelin basic protein, myelin oligodendrocyte glycoprotein, the proteolipid protein of multiple sclerosis and the CII collagen protein of rheumatoid arthritis, wherein the first antigenic polypeptide is an unbranched polypeptide, is not a homopolymer, is at least 15 amino acid residues long, and has an aqueous solubility at pH 4 to 10 of greater than 50 μg/ml;

depositing a second layer polyelectrolyte on the first layer polyelectrolyte to form a second layer; wherein a second layer comprises a second layer polyelectrolyte comprising a polycationic material or a polyanionic material having a molecular weight of greater than 1,000 and at least 5 charges per molecule, and a charge opposite that of the first layer polypeptide.

* * * * *